US008968237B2

(12) United States Patent
Ikemoto et al.

(10) Patent No.: US 8,968,237 B2
(45) Date of Patent: Mar. 3, 2015

(54) METHOD FOR INJECTING DRUG INTO LIVING BODY BY ELECTROSPRAYING AND DEVICE THEREOF

(75) Inventors: Kazuto Ikemoto, Niigata (JP); Takafumi Sakai, Saitama (JP); Kanako Koike, Saitama (JP); Satoshi Sakahara, Saitama (JP)

(73) Assignees: Mitsubishi Gas Chemical Company, Inc., Tokyo (JP); Saitama University, Saitama (JP)

( * ) Notice: Subject to any disclaimer, the term of this patent is extended or adjusted under 35 U.S.C. 154(b) by 374 days.

(21) Appl. No.: 13/145,269

(22) PCT Filed: Jan. 8, 2010

(86) PCT No.: PCT/JP2010/050164
§ 371 (c)(1),
(2), (4) Date: Jul. 19, 2011

(87) PCT Pub. No.: WO2010/082543
PCT Pub. Date: Jul. 22, 2010

(65) Prior Publication Data

US 2011/0275982 A1 Nov. 10, 2011

(30) Foreign Application Priority Data

Jan. 19, 2009 (JP) ................................ 2009-008798

(51) Int. Cl.
*A61M 5/30* (2006.01)
*H01R 13/645* (2006.01)
(Continued)

(52) U.S. Cl.
CPC .............. *H01R 13/6453* (2013.01); *H01R 9/03* (2013.01); *H01R 13/625* (2013.01); *H01R 13/748* (2013.01)
USPC .............................................. 604/68; 604/20

(58) Field of Classification Search
CPC . A61M 11/00; A61M 11/006; A61M 11/007; A61M 11/008; A61M 11/06
USPC .............. 604/20, 21, 23–26, 68–72, 289, 290
See application file for complete search history.

(56) References Cited

U.S. PATENT DOCUMENTS 5,112,804 A * 5/1992 Kowarski ....................... 514/5.9
5,200,393 A * 4/1993 Weiner ........................... 514/5.9
(Continued)

FOREIGN PATENT DOCUMENTS

EP 0 968370 B1 10/2005
JP 8-275709 A 10/1996
(Continued)

OTHER PUBLICATIONS

Zhang, Yi et al. Nasal Absorption Enhancement of Insulin by Sodium Deoxycholate in Combination With Cyclodextrins, Acta Pharmacol Sin, vol. 22, No. 11, pp. 1051-1056 (2001).*
(Continued)

*Primary Examiner* — Aarti B Berdichevsky
*Assistant Examiner* — Laura Schell
(74) *Attorney, Agent, or Firm* — Fitch, Even, Tabin & Flannery LLP

(57) ABSTRACT

The present invention provides a method whereby a drug can be conveniently injected into the living body, without sticking a needle, from a device that is not in contact with the living body, and a device therefor. Specifically provided is a method for injecting a peptide drug such as insulin, and a device therefor. No special consumables are needed except the drug solution or suspension. The method and device comprise injecting a drug into the living body by electrospraying a solution or suspension of the drug from a nozzle to which high voltage is applied and which is not in contact with the living body.

19 Claims, 2 Drawing Sheets

(51) Int. Cl.

| | |
|---|---|
| *H01R 9/03* | (2006.01) |
| *H01R 13/625* | (2006.01) |
| *H01R 13/74* | (2006.01) |

(56) References Cited

U.S. PATENT DOCUMENTS

| | | | | |
|---|---|---|---|---|
| 5,681,580 | A * | 10/1997 | Jang et al. | 424/449 |
| 5,997,848 | A | 12/1999 | Patton et al. | |
| 6,093,557 | A | 7/2000 | Pui et al. | |
| 6,685,967 | B1 | 2/2004 | Patton et al. | |
| 6,696,090 | B1 | 2/2004 | Nilsson et al. | |
| 7,255,102 | B2 * | 8/2007 | Modi | 128/200.14 |
| 8,142,391 | B2 * | 3/2012 | Mitchell | 604/68 |
| 2001/0001452 | A1 | 5/2001 | Moon et al. | |
| 2001/0007853 | A1 * | 7/2001 | Dimarchi et al. | 514/3 |
| 2006/0041248 | A1 | 2/2006 | Patton et al. | |
| 2009/0054831 | A1 * | 2/2009 | Mitchell | 604/24 |
| 2009/0233367 | A1 | 9/2009 | Ikemoto et al. | |

FOREIGN PATENT DOCUMENTS

| | | | | |
|---|---|---|---|---|
| JP | 10-501519 | T | 2/1998 | |
| JP | 2003/506472 | A | 2/2003 | |
| JP | 2003-159329 | A | 6/2003 | |
| WO | WO 98/56894 | A1 | 12/1998 | |
| WO | WO 01/12139 | * | 2/2001 | A61K 7/00 |
| WO | WO 01/12139 | A1 | 2/2001 | |
| WO | 2007/073527 | A2 | 6/2007 | |
| WO | 2007/073527 | A3 | 6/2007 | |
| WO | WO2007/132891 | A1 | 11/2007 | |

OTHER PUBLICATIONS

International Preliminary Report on Patentability dated Aug. 16, 2011, corresponding with International Application PCT/JP2010/050164.

International Search Report corresponding with International Application No. PCT/JP2007/060039 dated Jun. 12, 2007, (in English/Japanese), 4 pages.

Z. Takats et al., “Mass spectrometry sampling under ambient conditions wit ionization”, Science Oct. 15, 2004; 306 (5695): 471-3. (PubMed).

JB Fenn et al. “Electrospray ionization for mass spectrometry of large biomolecules”, Science Oct. 6, 1989; 246 (4926): 64-71. (PubMed).

Supplementary European Search Report dated Nov. 25, 2013, issued in EP Application 10731212.6.

Office Action issued by JPO on Sep. 10, 2013 in JP Appln. No. 2010-546616, including translation.

* cited by examiner

METHOD FOR INJECTING DRUG INTO LIVING BODY BY ELECTROSPRAYING AND DEVICE THEREOF

CROSS-REFERENCE TO RELATED APPLICATIONS

This is a U.S. National Phase of International Application PCT/JP2010/050164, filed Jan. 8, 2010, and claims the benefit of foreign priority under 35 U.S.C. §119 from Japanese Patent Application 2009-008789, filed Jan. 19, 2009, the entire disclosures of which are hereby incorporated herein by reference.

TECHNICAL FIELD

The present invention relates to a method for injecting a drug into a living body from a non-contact device and a device therefor. The present invention is a method for injecting a drug into a living body using electrospraying and a device therefor. Especially, it relates to a method for injecting a drug which is difficult to administer orally such as peptide and protein drugs, and a device therefor.

BACKGROUND ART

An injection is widely used as a method for injecting a drug into a living body. However, since an injection pricks a skin with a needle, a load such as a pain and skin degeneration is given to the administered patient, and this is seriously problematic especially for chronic disease such as diabetes that requires the injection for a long period of time. In addition, when a drug is administered by injection, a needle touches blood, and thus a problem arises such that infection with viral diseases or the like may be caused by accidental piercing of medical personnel. Further, fear of piercing with a needle is a big problem, and especially when the patient is an infant or a child, it frequently gives a mental shock. Moreover, when a rapid drug administration is required, for example, as a treatment at onset of anaphylaxis shock with an injection by a patient himself or a relative of a patient, it is highly possible that the treatment may be delayed by hesitation due to his fear of injection. Furthermore, considering that it is time-consuming to change needles in a situation where a drug has to be injected to an extremely large number of people like vaccination, a method without using a needle is required from the viewpoint of efficiency. Considering these points, needle-less syringes which push a drug from a small hole under high pressure have been developed. However, since the needle-less syringes also open a hole in the skin upon injection, it still has a problem of pain and skin degeneration similarly to the above syringe.

Among the drug administration methods, oral administration is the easiest, but peptide or protein drugs lose effect due to decomposition or denaturing by the action of gastric acid and digestive enzyme when passing through digestive tracts. For example, insulin which is a peptide drug widely used as an anti-diabetic drug is presently difficult to formulate for oral administration as an alternative to the injection. Recently, protein or peptide drugs such as antibodies tend to increase, and development of their administration methods alternative to the injection is important not only for treatment efficiency but also for quality of life (QOL) of patients.

In order to solve the problems such as physical pain, induration at injected site caused by repetitive administration and bacterial contamination, there has been proposed a method which uses insulin-containing fine particles in order that the drug is inhaled so as to be transferred from lungs into the body. Further, it has been proposed that the fine particles are electrically charged to increase delivery efficiency to lungs (Patent Documents 1 and 2). However, the production of fine particles leads to increase of steps, and thus is costly. Also, handling of solid fine particles is more difficult than handling of solutions, and thus a device for the former is also more complicated.

There has been proposed a method in which a solution is sprayed into a mouth so as to inject it into a living body (Patent Document 3). However, its effect cannot be said to be always satisfactory, and further since a gas such as Freon is used, there have been problems of cost and availability due to special consumables. Also, since Freon is one of the greenhouse gases, it is not preferable from the viewpoint of environment.

Electrospray is a means for spraying charged minute droplets of a liquid at high speed toward a counter electrode by applying a high voltage to a spray nozzle so as to collect electric charges at the tip of the nozzle, and passing the solution through the nozzle tip at which electric charges have been accumulated. The electrospray is widely known as, for example, an ionization method for mass analysis. Usually, a test sample to be analyzed is dissolved in a liquid and electrosprayed to perform ionization. Recently, there has been developed a method called desorption electrospray ionization, in which charged droplets generated by electrospray are allowed to hit a surface to mass-analyze the molecules of the surface (for example, Non-Patent Documents 1 and 2). Further, there have been developed methods in which the electrospray is used to coat a foundation or to spray agricultural chemicals (Patent Documents 3 and 4). However, the coating and spraying are nothing but a level of attaching to the surface.

In addition, there has been reported a method in which DNA is transferred into cells utilizing the electrospray. This method, which is one of the gene transfer methods, is a method in which a high voltage is applied to a suspension containing particles so as to spray it onto cells when it is passed through a capillary tip (Patent Document 6). Moreover, there has been developed a method in which whole cells are brought in contact with a substance to be transferred into the cells, the cells are electrosprayed with a liquid free from the substance to be transferred (Patent Document 7). However, the above method is a method for transferring a drug into cells, and is only shown to be capable of transferring a drug into a cell of an embryonic tissue, but there has not been known any method for transferring a drug through mucosa or skin into blood, subcutaneous tissue lymph or the like in the living body of actual animals.

Patent Document 1: Japanese Patent Laid-open (Kohyo) No. H10-501519
Patent Document 2: U.S. Pat. No. 6,696,090 specification
Patent Document 3: U.S. Pat. No. 7,255,102 specification
Patent Document 4: Japanese Patent Laid-open (Kohyo) No. 2003-506472
Patent Document 5: Japanese Patent Laid-open (Kokai) No. H08-275709
Patent Document 6: U.S. Pat. No. 6,093,557 specification
Patent Document 7: International publication No. WO2007/132891 pamphlet
Non-Patent Document 1: J. B. Fenn, M. Mann, C. K. Meng, S. F. Wong, C. M. Whitehouse, Science, 286, p 64-71, (1989).
Non-Patent Document 2: Z. Takats, J. M. Wiseman, B. Cologen, R. G. Cooks, Science, 306, p 471-473, (2004).

SUMMARY OF THE INVENTION

Problems to be Solved by the Invention

The object of the present invention is to provide a method for easily injecting a drug from a non-contact device into a living body without pricking with a needle and a device therefor. Especially, it is to provide a method for injecting a peptide drug such as insulin and a device therefor. In addition, another object is to preclude any special consumable except a solution or suspension of the drug.

Means for Solving the Problem

According to the present invention, a drug can be injected into a living body by electrospraying a solution or suspension of the drug. That is, the present invention can be achieved by the methods defined below.

(1) A device for injecting a drug into a living body, which comprises a nozzle for electrospraying a solution or suspension of the drug into the living body, in which a voltage is applied to the above nozzle so as to form, between the nozzle and the living body, a potential difference which is high sufficiently for injecting the electrosprayed drug into the living body.

(2) The device according to the above item (1), which comprises a high voltage power supply for applying a voltage to the above nozzle.

(3) The device according to the above item (2), which comprises a vessel containing the solution or suspension of the drug and a pump transferring the solution or suspension of the drug from the vessel to the above nozzle.

(4) The device according to the above item (1), which comprises a means for arranging the above nozzle in non-contact with the inner wall of an oral or nasal cavity.

(5) The device according to any one of the above items (1) to (4), wherein the inner diameter of the tip of the above nozzle is 0.02-3 mm, the voltage is applied to the nozzle to make the potential difference from the living body to be 1-30 kV, and the maximum electric current of the high voltage power supply that applies the above voltage is limited to 200 μA.

(6) The device according to the above item (1), wherein the drug is a drug containing a peptide or protein component.

(7) The device according to the above item (6), wherein the solution or suspension of the drug comprises one or more selected from the group consisting of a surfactant, a water-soluble polymer, a sugar, an alkali metal salt, an alkaline earth metal salt and a zinc salt.

(8) The device according to the above item (6), wherein the drug is insulin.

(9) A method for injecting a drug into a living body, in which a solution or suspension of the drug is electrosprayed into the living body from a nozzle to which a voltage is applied so as to form, between the nozzle and the living body, a potential difference which is high sufficiently for injecting the drug into the living body.

(10) The method according to the above item (9), wherein the solution or suspension of the drug is electrosprayed in an oral or nasal cavity so as to inject the drug into the living body via an oral or nasal mucosa.

(11) The method according to the above item (7) or (8), wherein the inner diameter of the tip of the above nozzle is 0.02-3 mm, the voltage is applied to the nozzle to make the potential difference from the living body to be 1-30 kV, and the maximum electric current of the high voltage power supply that applies the above voltage is limited to 200 μA.

(12) The method according to the above item (9), wherein a drug to be injected is a drug containing a peptide or protein component.

(13) The method according to the above item (12), wherein the solution or suspension of the drug comprises one or more selected from the group consisting of a surfactant, a water-soluble polymer, a sugar, an alkali metal salt, an alkaline earth metal salt and a zinc salt.

(14) The method according to the above item (12), wherein the drug to be injected comprises deoxycholic acid or a salt thereof.

(15) The method according to the above item (12), wherein the drug to be injected is insulin.

(16) A drug composition which is prepared for being injected into a living body by electrospraying, said drug composition comprising a drug containing a peptide or protein component which is dissolved or suspended in a solvent or dispersion medium.

(17) The drug composition according to the above item (16), wherein the solvent comprises one or more selected form the group consisting of water, ethanol, isopropanol dimethylsulfoxide, and oils and fats.

(18) The drug composition according to the above item (17), which comprises a surfactant, a water-soluble polymer, a sugar, an alkali metal salt, an alkaline earth metal salt and a zinc salt.

(19) The drug composition according to the above item (17), which comprises deoxycholic acid or a salt thereof.

Effect of the Invention

The present invention can be used as an alternative to the syringe when a drug which is difficult in oral administration is administered into the living body, but does not need to prick a skin with a needle. Therefore, fear associated with the injection is eliminated, and the risk of infection and skin degeneration by the needle are greatly decreased. Also, no special consumables such as a gas cylinder are required. Further, the present invention enables administration of peptide drugs which have been particularly difficult to be administered orally.

BRIEF DESCRIPTION FOR DRAWINGS

MODE FOR CARRYING OUT THE INVENTION

The present invention is a method for injecting a drug into a living body by electrospray and a device therefor, in which the drug is injected into the living body by applying a high voltage to a nozzle so that a liquid is atomized electrostatically from the nozzle to cause spraying, and thus sprayed to the living body which has a potential difference from the liquid, and a device therefor. Concretely, it is a method for injecting a drug into a living body by electrospraying a solution or suspension of a drug from a nozzle which is not in contact with the living body and to which a high voltage is applied, and a device therefor. Organisms to which a drug can be injected according to the present invention for injecting a drug into the living body include animals such as mammals including human and birds.

Figure 1:
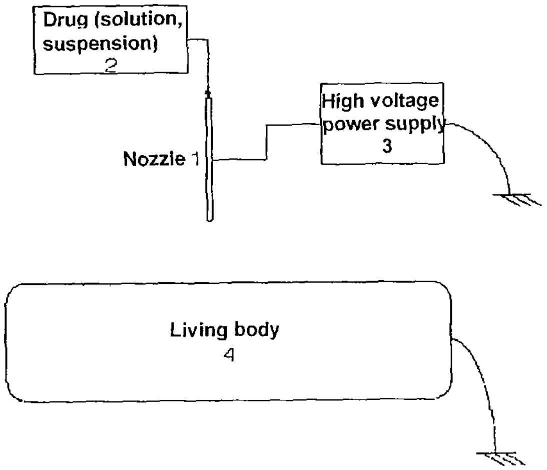
FIG. 1 is a schematic view showing the device of the present invention and the method of use thereof.

FIG. 1 shows a schematic view of the present invention and usage thereof. A solution or suspension 2 of a drug is supplied to a nozzle 1. The nozzle is arranged to have a potential difference from a living body 4 by use of a high voltage power supply 3. Since a high voltage is applied to the solution or suspension of the drug at the nozzle, it is electrically charged at the nozzle tip and sprayed as minute droplets so as to be selectively injected into the living body having a potential difference. The site to the drug is injected includes skin, oral cavity, eyes or nasal cavity such as external nostril. Particularly effective sites to which drug is injected are oral and nasal cavities.

When the inner diameter of the tip of the nozzle to be used is too small, clogging with a liquid is easy to occur, and when it is too large, concentration of an electric field is hard to occur, and thus the inner diameter is preferably 0.02-3 mm and particularly preferably 0.05-1 mm. As a material for the nozzle, a plastic, metal or glass can be used. Among these, plastics and metals are preferable, and concretely exemplified are polyether ether ketone, polyethylene, polypropylene, Teflon (registered trade mark), polycarbonate, polystyrene, silicone resin, synthetic rubber, acrylic resin, vinyl chloride resin, nylon, ABS, methylpentene resin, polyurethane resin, epoxy resin, stainless steel, aluminum, and titanium.

The potential difference between the site of the nozzle to which a voltage is applied and the living body is desirably 1-30 kV. When the potential difference is not less than 1 kV, electrospray can easily occur. When it is not more than 30 kV, the device may be decreased in cost due to easiness of insulation, and also discharge becomes difficult to occur so that the possibility of spark discharge is extremely suppressed. Meanwhile, in the present invention, polarity of the voltage to be applied to the nozzle may be either positive or negative.

It is desired that the maximum electric current of the high voltage power supply is limited to 200 μA. When the maximum electric current of the high voltage power supply is limited to 200 μA, any electric current exceeding 200 μA does not flow into the living body so that the living body feels no pain or stimulus such as electric shock.

Figure 2:
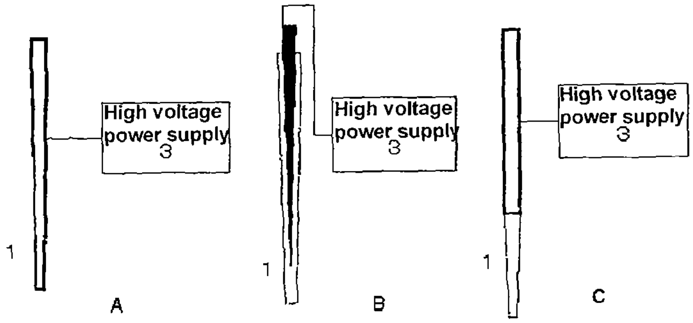
FIG. 2 shows nozzles.

The method for applying a voltage to a solution or suspension of the drug includes a method in which an electrically conductive nozzle is used so that a voltage is applied to the whole nozzle, a method in which an electrically insulating nozzle is used and provided in the inside thereof with an electrode to which a voltage is applied, and a method in which the nozzle tip is made of an electrically insulating material and the site to which a voltage is applied is separated from the tip. FIG. 2 shows concrete nozzle forms.

FIG. 2A shows that the whole nozzle is made of an electrically conductive material such as a metal, and a voltage application is performed by contact of the solution or suspension of the drug therewith. The outside of the nozzle may be coated with an electrically insulating material. FIG. 2B is a schematic view of the case where a voltage applying electrode is inserted into the inside of the nozzle. This is one of the methods for applying a voltage to the solution or suspension of the drug when the nozzle itself is made of an electrically insulating material. FIG. 2C shows that the nozzle tip is made of an electrically insulating material, a part connecting with the high voltage power supply is made of an electrically conductive substance, and the solution or suspension of the drug is electrically charged when it passes through the electrically conductive part. This method cannot be used when the solution or suspension of the drug is electrically insulating. However, most of the drugs contain water as a constituent, and thus can be used without any problems.

In the present invention, any of the above methods can be used. Also, the form of the nozzle is not particularly limited as long as it causes concentration of electric field so as to enable electrospraying, and a tubular form is easy to use and preferable.

The distance between the nozzle tip and the living body is preferably 1-80 mm and particularly preferably 2-30 mm. When the distance between the nozzle tip and the living body is less than 1 mm, spark discharge easily occurs, and thus the voltage has to be lowered, and when it is not less than 80 mm, speed of droplets is decreased due to air resistance so that the amount of the drug to be injected is extremely decreased.

Figure 3:
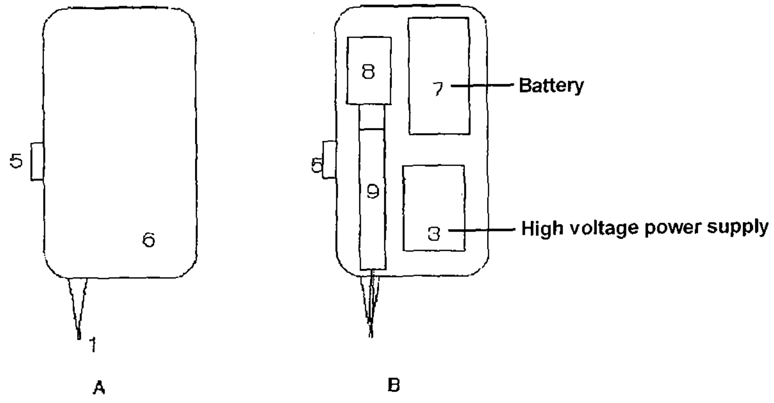
FIG. 3 shows an example of an arrangement of the device of the present invention.

FIG. 3 exemplifies an arrangement of the device of the present invention. FIG. 3A shows an appearance, and FIG. 3B shows an arrangement of the inside parts. In FIG. 3A, a nozzle 1 is connected to a housing 6, and a switch 5 is attached to the housing 6. FIG. 3B shows the inside structure of the device. Inside the housing, there exist a high voltage power supply 3, a vessel 9, a battery 7, and a pump 8. The battery 7 supplies electricity to the high voltage power supply 3 and the pump 8. The output of the high voltage power supply 3 is connected to the nozzle 1 inside the housing so that a high voltage is applied to the nozzle 1. The vessel 9 contains a solution or suspension to be electrosprayed. The pump 8 is connected to the vessel 9, and pumps the solution or suspension of the drug from the inside of the vessel to the nozzle. The order of connection of the vessel and the pump may differ according to the type of the pump. For example, when the vessel is in a cylinder form and the pump is of a type that pushes its plunger, the vessel is connected to the nozzle. Conversely, when the pump is a tube pump which sucks up the solution or suspension from the vessel, the pump is connected to the nozzle.

Figure 4:
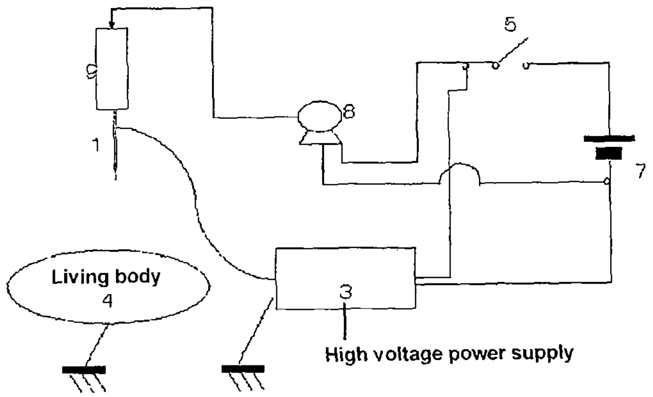
FIG. 4 is a connection diagram of the device of the present invention.

FIG. 4 shows the wiring of the device of the present invention. FIG. 4 is a schematic view omitting parts such as relays, resistances, capacitors and semi-conductors that may be required in actual use. In FIG. 4, the wiring is structured so that the power of the battery 7 is supplied to the high voltage power supply 3 and the pump 8 via the switch 5 whilst the high voltage power supply 3 and the pump 8 are powered simultaneously. The high voltage power supply 3 increases the electric power supplied from the battery, and supplies the high voltage to the nozzle 1. The nozzle 1 applies the high voltage to the solution or suspension of the drug which is supplied from the vessel 9 by the pump 8, so as to perform electrospray into the living body. The living body 4 is required to be at the ground potential in order to create a potential difference from the high voltage power supply 3, and an easy method therefor is to connect the living body 4 to the ground of the high voltage power supply 3. A cable or the like can be used for the connection. Also, when a person who performs electrospray injects the electrosprayed drug into himself, the living body can be kept at the ground potential if a part of the housing is made electrically conductive and connected to the ground of the high voltage power supply and touched by him.

Electrospray can be performed without the living body being connected with the ground, but is preferably performed with the living body being connected with the ground. If the living body is connected with the ground of the high voltage power supply, no electric charge accumulates in the living body, thereby eliminating problems which may arise due to the change in potential of the living body, for example, failure to electrospray or electrostatic shock to the living body.

When electrospray is performed in oral cavity, it is preferable that a mouth piece is attached, and a nozzle is disposed inside the mouse piece.

The device of the present invention can inject any of low molecular weight drugs and high molecular weight drugs. Particularly, peptide or protein drugs which are difficult in oral administration can be injected by the device of the present invention. Examples of the peptide and protein drugs include peptide hormone, antibody and vaccine, and concrete examples thereof include insulin, insulin-like growth factors, erythropoietin, interferon, interleukin, interleukin-1 receptor, calcitonin, parathyroid hormone (PTH-34), α-1 antitrypsin, growth hormone releasing factor, heparin, influenza virus vaccine, deoxynuclease and amylin. The drugs other than the peptide and protein drugs include adrenaline. Among these, it is expected that the device of the present invention is favorably used as an alternative to the syringe for administration of insulin which is a therapeutic drug for diabetes which a particularly large number of patients suffer from.

The solution or suspension of the drug used in the device of the present invention may comprise a drug and a solvent or dispersion medium only or may further comprise another component. Also, such a solution or suspension of the drug may be prepared as a drug composition in a form suitable for injecting the drug into the living body with electrospraying according to the method of the present invention, by dissolving or suspending a drug containing a peptide or protein component in a solvent or dispersion medium, and optionally storing the resultant in an appropriate vessel.

The solvent or dispersion medium for preparing the solution or suspension is not particularly limited, and water, ethanol, isopropanol, dimethylsulfoxide, fats and oils etc. can be used, as required. Particularly, water is preferable. When water is used, the pH and the like are not particularly limited as long as stability of the drug is ensured.

In order to improve efficiency and stability of the injection of the drug into a living body, it is effective that a solution or suspension of the drug comprises a component other than the drug and the solvent or dispersion medium. Particularly, in order to improve efficiency of injection, any of surfactants, water-soluble polymers, sugars, alkali metal salts, alkaline earth metal salts and zinc salts can be used. Examples of the surfactants include bile salts such as taurocholate, glycocholate and deoxycholate, fusidates such as taurodihydrofusidate, and biocompatible surfactants (for example, polyoxyethylene alkylethers such as polyoxyethylene lauryl ether) such as Tween (registered trademark) and Laureth-9. Examples of the water-soluble polymers include polyethylene glycol, alginic acid, agarose and polyvinyl alcohol, examples of the sugars include galactose, D-mannose, sorbose, lactose, trehalose, cyclodextrin, raffinose, maltodextrins, dextrans, mannitol, xylotol and lactose. Also, examples of the alkali metal salts, alkaline earth metal salts and zinc salts include sodium chloride, potassium chloride, calcium chloride, sodium phosphate, potassium phosphate, zinc chloride, sodium citrate and sodium ascorbate. More preferably one is deoxycholic acid or a salt thereof. Addition amount of these is preferably 0.1 mg/mL to 300 mg/mL and more preferably 1 mg/mL to 200 mg/mL relative to the whole solution or suspension of the drug. A combination of deoxycholic acid or a salt thereof with a polyoxyethylene alkyl ether such as polyoxyethylene lauryl ether is effective, and this also enables the addition amount to be lower than using alone. The addition amount of each component is preferably 0.05 mg/mL to 100 mg/mL and more preferably 0.5 mg/mL to 50 mg/mL.

The amount of the drug relative to the whole solution or suspension of the drug can be about 0.01 mg/mL to about 500 mg/mL. It is preferably 0.1-100 mg/mL. When the drug is insulin, it is preferably 0.1 mg/mL to 10 mg/mL and more preferably 1 mg/mL to 5 mg/mL relative to the whole solution or suspension of the drug.

A mechanism of uptake into the living body resulting from the injection of the drug with the device of the present invention is assumed as follows. First, when a solution or suspension containing the drug is passed through a nozzle to which a high voltage is applied, it is electrically charged and broken minutely so as to become charged droplets. Further, the charged droplets are sprayed at high-speed towards the surface of the living body with a potential difference. In this instance, evaporation of a solvent component of the droplets proceeds together with increase of their surface area, so that the drug is concentrated. Since the surface (mucosa, skin and lung) of the living body is electrically charged, the charged droplets are attached thereto with higher efficiency than ordinary droplets. Also, they hit the surface of the living body at high speed due to electric attraction to the living body. Thus, it is considered that they are easier to be taken up into the living body than the ordinary droplets. In case of electrospraying to a mouth or nose, there may present a route of uptake from the lungs as well as the mucosa of the corresponding site. Also, since droplets generated by spraying are electrically charged, there is a great possibility that the uptake is promoted electrically. Moreover, if the drug is highly concentrated in this instance, the difference in osmotic pressure is expected to facilitate the passing through skin, mucosa or the like. Further, an effect of further promoting the uptake can be expected by coexistence of a reagent which promotes the uptake.

The device of the present invention is characterized in that small droplets are formed, and thus are considered to cause little irritation, and it is also effective for injecting, namely, administrating a drug into a surface tissue which is wounded by inflammation, burn or frostbite. By using the device of the present invention, the drug permeates into the inside of the tissue, and it is expected that the drug effectively acts compared to the conventional application. By administrating a growth factor or steroid to a burn according to the method of the present invention, shortening of recovery time and decrease in the amount to be used can be expected. Further, the device of the present invention is effective for injecting a drug into a tissue during an abdominal operation.

EXAMPLE

The following Examples are presented by way of exemplification, and the present invention is in no way restricted to these Examples.

Example 1

(1) The Device for the Experiment

Figure 5:
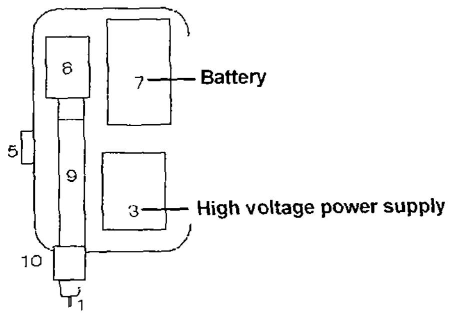
FIG. 5 is a schematic view of the device used for the experiment.

The schematic view of the device used for the experiment is shown in FIG. 5. It is a small device having a high voltage power supply 3 inside the housing, and a nozzle tip is made of stainless steel with an inner diameter of 0.18 mm and an outer diameter of 0.36 mm and electrically connected to the high voltage power supply 3. Electric power is supplied from a battery 7 to the high voltage power supply 3 and a pump 8. A liquid is supplied at a rate of 120 μl/min from a vessel 9 of the device. A polyethylene cover 10 which prevents electric shock and functions as a mouth piece is arranged on the nozzle 1. Also, a part of the housing is grounded, and thus a person using the device is set to the ground potential.

(2) Preparation of a Solution for Spraying

Insulin (manufactured by Sigma Aldrich) was added to pure water, and mixed with an aqueous solution of sodium deoxycholate (manufactured by Wako). The final concentration was set to 3.4 mg/ml insulin and 100 mg/ml sodium deoxycholate to obtain a solution for spraying.

(3) Electrospray of Insulin

Eight (8) week old female Wistar rats were used as experimental animals. The rat was anesthetized by intra-abdominal administration of a 1 ml/kg Nembutal (manufactured by Dainippon Sumitomo Pharma Co., Ltd.), and placed on an aluminum tray. While the rat was held by the left hand, a voltage of +10 kV was applied to the nozzle so that the above drug solution was electrosprayed into an oral cavity for 30 seconds. In this instance, the electric current flowing into the high voltage power supply was about 100 μA.

After the completion of the electrospraying, blood was collected from the tail vein of the rat over time, and the blood glucose level measurement device MEDISAFE MINI GR-102 (manufactured by TERUMO CORPORATION, JAPAN) was used to measure the blood glucose level.

The above insulin injection experiment was made on three rats, and the change in blood glucose level is shown in Table 1. The value is a relative value, assuming that the initial value (about 160 mg/dl) of blood glucose level was 100%.

The blood glucose level an hour after the completion of electrospraying was decreased to 62-71% of the initial value.

TABLE 1

Change in blood glucose level of rats

| Time (h)* | Blood glucose level (%) Rat 1 | Rat 2 | Rat 3 |
|---|---|---|---|
| 0 | 100 | 100 | 100 |
| 0.5 | 83 | 84 | 83 |
| 1.0 | 62 | 71 | 67 |
| 1.5 | 74 | 81 | 88 |
| 2.0 | 78 | 92 | 83 |

*The time when electrospraying was completed was 0 h.

Comparative Example 1

An aqueous 100 mg/ml sodium deoxycholate solution free from insulin was prepared, and the experiment was performed in the same manner as in Example 1 except using this solution instead of the above solution for spraying. The results thereof are shown in Table 2. No lowering of blood glucose level was observed.

Comparative Example 2

The same procedure as in Example 1 was performed except that no voltage was applied to the nozzle. Electrospray did not occur, and the drug solution was dropped in the oral cavity. The results are shown as a relative value in Table 2. The blood glucose level one hour after the completion of electrospraying was 88% of the initial value, and the lowering of blood glucose level was smaller than Example 1.

TABLE 2

Change in blood glucose level of rats

| Time (h)* | Blood glucose level (%) Comparative Example 1 | Comparative Example 2 |
|---|---|---|
| 0 | 100 | 100 |
| 0.5 | 127 | 101 |
| 1.0 | 106 | 88 |
| 1.5 | 104 | 88 |
| 2.0 | 102 | 85 |

*The time when electrospraying was completed was 0 h.

Example 2

(1) Preparation of the Fluorescence-Labeled Insulin Solution

A 100 mg of insulin (manufactured by Sigma Aldrich) was dissolved in a 50 ml aqueous solution of 1.7% sodium carbonate (manufactured by Wako) and 2.8% sodium hydrogen carbonate (manufactured by Wako). Further, it was mixed with 1 ml of a dimethylsulfoxide solution of 7.8 mg/ml fluorescene-4-isothiocyanate (FICT) (manufactured by DOJINDO LABOLATORIES). The mixture was allowed to react for an hour at 37° C., and freeze-dried to synthesize a fluorescence-labeled insulin. Subsequently, an aqueous solution containing 4 mg/ml (insulin equivalent) of the above fluorescence-labeled insulin and 100 mg/ml of sodium deoxycholate was prepared.

(2) Experiment for Electrospraying

A stainless steel tube with an inner diameter of 0.18 mm and an outer diameter of 0.36 mm was used as a nozzle. A high voltage power supply was connected thereto, and a voltage of +10 kV was applied. A pig skin (thickness: about 4 mm) (manufactured by Funakoshi Co., Ltd.) already shaved was placed on an electrode set to ground potential, and the above solution was electrosprayed for 15 seconds with a distance of 2 cm between the ground electrode and the nozzle at a flow rate of 100 μl/min. In this instance, the electric current flowing into the high voltage power supply was 10 μA or lower. Then, the pig skin was washed with a physiological saline for three times or more, and was observed using a microscope TE-2000S (manufactured by NIKON) with objective lens×4 and a high voltage mercury lamp as a light source equipped with a fluorescence filter GFP block (manufactured by NIKON).

Figure 6:
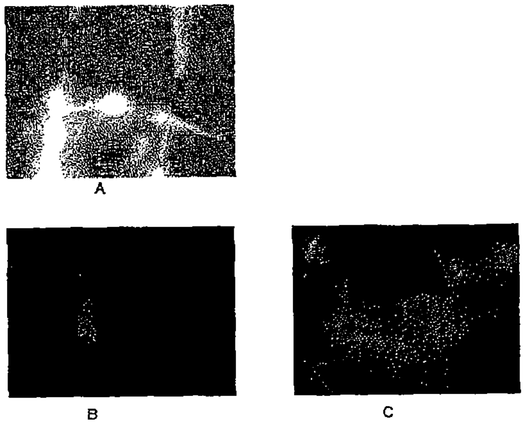
FIG. 6 is a fluorescent microscopic photograph of a pig skin used for the experiment for injecting fluorescence-labeled insulin.

The fluorescent microscopic photograph is shown in FIG. 6A. After electrospraying, the whole skin of the pig skin emitted fluorescence, and some scattering parts thereof emitted fluorescence strongly. This fluorescence did not disappear even after it was further washed with a physiological saline for three times or more.

Comparative Example 3

The same procedure as in Example 2 was performed except that no voltage was applied to the nozzle. The fluorescent microscopic photographs of a pig skin before and after treatment were shown in FIG. 6B and FIG. 6C, respectively.

In the untreated pig skin, part of hairs showed a slight fluorescence. Also, in the pig skin to which no voltage was applied, only a little amount of affixed matters emitted fluorescence, and the fluorescence intensity was weaker than Example 2.

Example 3

The experiment was performed in the same manner as in Example 1 except that an aqueous solution comprising 2.5 mg/ml insulin, 10 mg/ml sodium deoxycholate and 10 mg/ml polyoxyethylene lauryl ether was used as a solution for spraying. The blood glucose level was 43 after 1.5 hours and 29 after 2 hours when the initial value was set to 100. Insulin was able to be efficiently injected into a living body using a small amount of sodium deoxycholate in combination with a polyoxyethylene lauryl ether.

Example 4

The experiment was performed in the same manner as in Example 1 except that an aqueous solution comprising 2.5 mg/ml insulin and 100 mg/ml sodium deoxycholate was used as a solution for spraying. The blood glucose level was 46 after 1.5 hours and 57 after 2 hours when the initial value was set to 100. By lowering the insulin concentration, uniformity of the solution was increased.

Comparative Example 4

The experiment was performed in the same manner as in Example 1 except that an aqueous solution comprising 3.4 mg/ml insulin and 50 vol % dimethylsulfoxide was used as a solution for spraying. No lowering of blood glucose level was observed.

Comparative Example 5

The experiment was performed in the same manner as in an Example 1 except that an aqueous solution comprising 3.4 mg/ml insulin and 140 mg/ml sodium dodecylsulfate was used as a solution for spraying. No lowering of blood glucose level was observed.

Comparative Example 6

The experiment was performed as in the same manner as in Example 1 except that an aqueous solution comprising 2.5 mg/ml insulin and 10 mg/ml polyoxyethylene lauryl ether was used as a solution for spraying. No lowering of blood glucose level was observed.

INDUSTRIAL APPLICABILITY

The present invention can be used for administrating a drug into a living body such as of human and is effective in the field of medical treatment and medical devices.

DESCRIPTION OF SYMBOLS

1. Nozzle
2. Solution or suspension of the drug
3. High voltage power supply
4. Living body
5. Switch
6. Housing
7. Battery
8. Pump
9. Vessel
10. Polyethylene cover

The invention claimed is:

1. A method for injecting a drug in a solution or suspension dosage form into a living body, in which the solution or suspension of the drug is electrosprayed into the living body from a nozzle to which a voltage is applied so as to form, between the nozzle and the living body, a potential difference which is sufficiently high for injecting the drug into the living body, wherein the solution or suspension of the drug to be injected comprises deoxycholic acid or a salt thereof and a polyoxyethylene alkyl ether provided that a solution or suspension which is electrically insulating is excluded; and the entire nozzle or a part of the nozzle is insulated, provided that a voltage is applied to the solution or suspension.

2. The method according to claim 1, wherein the solution or suspension of the drug is electrosprayed in an oral or nasal cavity so as to inject the drug into the living body via an oral or nasal mucosa.

3. The method according to claim 1, wherein the inner diameter of the tip of the above nozzle is 0.02-3 mm, the voltage is applied to the nozzle to make the potential difference from the living body to be 1-30 kV, and the maximum electric current of the high voltage power supply that applies the above voltage is limited to 200 μA.

4. The method according to claim 1, wherein a drug to be injected is a drug containing a peptide or protein component.

5. The method according to claim 4, wherein the drug to be injected is insulin.

6. The method according to claim 1, wherein the polyoxyethylene alkyl ether comprises polyoxyethylene lauryl ether.

7. The method according to claim 1, wherein the solution or suspension contains deoxycholic acid or a salt thereof in an amount of 0.05 mg/mL to 100 mg/mL and contains a polyoxyethylene alkyl ether in an amount of 0.05 mg/mL to 100 mg/mL.

8. The method according to claim 1, wherein the solution or suspension contains deoxycholic acid or a salt thereof in an amount of 0.5 mg/mL to 50 mg/mL and contains a polyoxyethylene alkyl ether in an amount of 0.5 mg/mL to 50 mg/mL.

9. The method according to claim 1, wherein the nozzle is comprised of electrically conductive material and has an interior surface and an exterior surface, and the exterior surface is electrically insulated.

10. The method according to claim 1, wherein the nozzle has an electrode and a body having an interior volume, the body is comprised of electrically insulating material, and the electrode is provided in the interior of the nozzle to which the voltage is applied so that a voltage is applied to the solution or suspension.

11. The method according to claim 1, wherein the nozzle has a tip and is comprised of an electrically conductive material, and the tip is electrically insulated.

12. A method for electrospraying a drug into a living body by electrospraying an aqueous solution or suspension of the drug through a nozzle to atomize it electrostatically, wherein a voltage is applied to the nozzle so as to form, between the nozzle and the living body, a sufficiently high potential difference for injecting the drug into the living body, wherein the solution or suspension of the drug to be injected comprises deoxycholic acid or a salt thereof and a polyoxyethylene alkyl ether provided that a solution or suspension which is electrically insulating is excluded; and the entire nozzle or a part of the nozzle is insulated, provided that a voltage is applied to the solution or suspension.

13. The method according to claim 6, wherein the drug is insulin.

14. The method according to claim 6, wherein the polyoxyethylene alkyl ether comprises polyoxyethylene lauryl ether.

15. The method according to claim 12, wherein the solution or suspension contains deoxycholic acid or a salt thereof in an amount of 0.05 mg/mL to 100 mg/mL and contains a polyoxyethylene alkyl ether in an amount of 0.05 mg/mL to 100 mg/mL.

16. The method according to claim 12, wherein the solution or suspension contains deoxycholic acid or a salt thereof in an amount of 0.5 mg/mL to 50 mg/mL and contains a polyoxyethylene alkyl ether in an amount of 0.5 mg/mL to 50 mg/mL.

17. The method according to claim 12, wherein the nozzle is comprised of electrically conductive material and has an interior surface and an exterior surface, and the exterior surface is electrically insulated.

18. The method according to claim 12, wherein the nozzle has an electrode and a body having an interior volume, the body is comprised of electrically insulating material, and the electrode is provided in the interior to which the voltage is applied so that a voltage is applied to the solution or suspension.

19. The method according to claim 12, wherein the nozzle has a tip and is comprised of an electrically conductive material, and the tip is electrically insulated.

* * * * *

UNITED STATES PATENT AND TRADEMARK OFFICE

CERTIFICATE OF CORRECTION

PATENT NO. : 8,968,237 B2
APPLICATION NO. : 13/145269
DATED : March 3, 2015
INVENTOR(S) : Kazuto Ikemoto et al.

It is certified that error appears in the above-identified patent and that said Letters Patent is hereby corrected as shown below:

On the title page item [30] Foreign Application Priority Data, the correct priority number is (JP) 2009-008789

In the Claims

Claim 13 should read:

The method according to claim 12, wherein the drug is insulin.

Claim 14 should read:

The method according to claim 12, wherein the polyoxyethylene alkyl ether comprises polyoxyethylene lauryl ether.

Signed and Sealed this
Fifteenth Day of September, 2015

Michelle K. Lee
*Director of the United States Patent and Trademark Office*